United States Patent [19]

Schwinn et al.

[11] 4,405,603

[45] Sep. 20, 1983

[54] METHOD FOR RENDERING FACTORS IX AND X HEPATITIS-SAFE WITH CALCIUM IONS

[75] Inventors: Horst Schwinn; Norbert Heimburger, both of Marburg/Lahn; Gerhardt Kumpe, Wetter; Wilfried Wormsbächer, Kirchhain, all of Fed. Rep. of Germany

[73] Assignee: Behringwerke Aktiengesellschaft, Marburg/Lahn, Fed. Rep. of Germany

[21] Appl. No.: 324,872

[22] Filed: Nov. 25, 1981

[30] Foreign Application Priority Data

Nov. 29, 1980 [DE] Fed. Rep. of Germany ....... 3045153

[51] Int. Cl.$^3$ ............................................. A61K 35/14
[52] U.S. Cl. ..................................................... 424/101
[58] Field of Search ......................................... 424/101

[56] References Cited

U.S. PATENT DOCUMENTS 4,327,086 4/1982 Fukushima et al. ............... 424/101

Primary Examiner—Sam Rosen
Attorney, Agent, or Firm—Curtis, Morris & Safford

[57] ABSTRACT

What is disclosed is a method for making a preparation containing blood clotting Factors IX and/or X virtually hepatitis-safe by warming said peparation in the presence of calcium ions and in the further presence of an amino acid and/or a saccharide or sugar alcohol.

3 Claims, No Drawings

METHOD FOR RENDERING FACTORS IX AND X HEPATITIS-SAFE WITH CALCIUM IONS

The invention relates to a process for the production of a virtually hepatitis-safe preparation of the blood-clotting Factors IX and X by warming in the presence of calcium ions, if appropriate in the additional presence of an amino acid and/or a saccharide or sugar alcohol.

Blood-clotting is a complex function which proceeds in stages and is initiated by various physiological as well as pathological causes and the course of which depends on about 20 promoting and inhibiting factors. As a result of a reduction or increase in these blood-clotting factors, disorders of blood-clotting arise and some of these manifest themselves as diseases.

Factor IX and X-containing preparations, which are useful for treating disturbances as caused by deficiencies of these factors, are known.

These preparations are not free from the risk of transmitting hepatitis.

Albumin is regarded as hepatitis-safe, if it is heated in aqueous solution at 60° C., in the presence of stabilizers (Gellis, S.S. et al., J. Clin. Invest. (1948) 27, 239). It may therefore be assumed that a Factor IX and/or X concentrate which has been heated in the presence of suitable stabilizers is also hepatitis-safe.

German Offenlegungsschrift No. 2,916,711 has disclosed a process for the heat-stabilization of other clotting factors in aqueous solution by adding an aminoacid and a monosaccharide or oligosaccharide or a sugar alcohol.

However, a complete inactivation of the Factors IX and X, when proceeding in the above manner, cannot be avoided.

Thus, there was still the object of discovering a process for the heat-stabilization of aqueous solutions of Factor IX and/or X concentrates, in order to reduce the losses in activity.

Surprisingly, it has now been found that an aqueous solution of Factor IX and/or Factor X can be heat-stabilized by the addition of calcium ions. Hitherto, no process for the stabilization of these factors against inactivation by heat was known.

The invention relates to a process for the production of a virtually hepatitis-safe preparation of blood-clotting Factors IX and/or X by warming in the presence of calcium ions, if appropriate in the additional presence of an aminoacid and/or a saccharide or sugar alcohol.

The calcium ions are added in a concentration of from 0.05 to 2.0, preferably 0.4 to 0.6, moles/l.

Examples of suitable salts donating calcium ion are:
calcium chloride ($CaCl_2$),
calcium acetate ($Ca(Ac)_2$),
calcium nitrate, as well as any water-soluble calcium salts of saccharic acids such as gluconic acid, lactonic acid etc.

$CaCl_2$ and $Ca(Ac)_2$ are preferably used.

In the presence of calicum ions of this type, the aqueous solution of the clotting factors can be heated for such a long period that, according to the present state of knowledge, the transmission of hepatitis pathogens can be virtually excluded. This applies especially in conjunction with precipitation processes in which the active ingredient remains in the supernatant liquid and the hepatitis viruses can be separated off together with the insoluble precipitate. A preparation which has been kept for at least 10 hours at about 60° C. in aqueous solution is nowadays regarded as virtually hepatitis-safe, in particular if the starting material used is human tissue in which hepatitis viruses cannot be detected by means of a test of the third generation.

In a particularly preferred embodiment of the invention, 0.05 to 2.0 moles/l of one of the soluble calcium salts, preferably 0.4 to 0.6 mole/l of $CaCl_2$ and, if appropriate, 1.0 to 3.0 moles/l of at least one of the aminoacids glycine, $\alpha$- or $\beta$-alanine, hydroxyproline, proline, glutamine or $\alpha$-, $\beta$- or $\gamma$-aminobutyric acid, preferably glycine, and 20 to 60% by weight of monosaccharides or oligosaccharides or sugar alcohols, preferably 1.0 to 3.0 moles/l of glycine and 20 to 60% by weight of sucrose, are added to a solution containing Factor IX and/or Factor X, preferably a plasma fraction or placenta fraction, the mixture is heated to a temperature of between 30° C. and 100° C., preferably 60° C. to 100° C., and held at this temperature for 1 minute to 48 hours, preferably about 10 hours, the shortest time being associated with the highest temperature, and vice versa. To obtain a maximum yield, the pH value must be matched specifically to the individual clotting factors present in the solution. In general, a pH value within the limits of 6.5 and 8.0 should be maintained. A virtually hepatitis-safe preparation of Factor IX and/or Factor X is obtained.

Depending on the solubility of the calcium salt, the aminoacid or the carbohydrate, the values of 0.3 and 3.0 moles/l or 60% by weight respectively can be extended to higher concentrations, if the calcium salt, the aminoacid or the carbohydrate have a correspondingly higher solubility at the desired temperature. The heat treatment can also be carried out in several successive steps.

When the preferred combination of $CaCl_2$ with glycine and sucrose is used, a hepatitis-safe preparation is obtained by heating under the following condition: heating for 10 to 20 hours at 60° to 70° C. in the presence of $CaCl_2$ in a concentration from 0.4 to 0.6 moles/l, sucrose in a concentration from 40 to 60% by weight and of glycine in a concentration from 1.0 to 2.5 moles/l, at a pH value from 6.8 to 8.0.

As can be seen in the Table, Factors IX and X are stabilized against the action of heat by calcium ions.

TABLE

Effect of calcium ions on the stability of the clotting factors

| Stabilizers | Clotting factor (U/ml) | | | |
|---|---|---|---|---|
| | IX | | X | |
| | Before heating | After heating | Before heating | After heating |
| Sucrose 60% by weight Glycine 2 moles/l | 50 | 0 | 40 | 0 |
| $Ca^{2+}$ 0.5 mole/l Sucrose 60% by weight Glycine 2 moles/l | 50 | 48 | 40 | 35 |

The recovery and purification of the clotting factors from the heated solution can be carried out by precipitation with 30–45% weight/volume of ammonium sulfate and adsorption of the supernatant liquid on 0.4 to 1.0% weight/volume of Ca phosphate.

Advantageously, the starting fractions are those in which the factor to be stabilized has been enriched according to the cited process.

Due to the knowledge of the methods for the determination of the substances concerned, those skilled in the art are familiar with monitoring the measures for the enrichment and purification of Factor IX or X. Using these monitoring methods, the process conditions can be controlled with regard to a satisfactory yield and a satisfactory purity of the product.

To obtain a hepatitis-safe concentrate of Factors IX and X, the starting material used is a fraction such as is obtained, for example, by the process of Soulier et al., Thrombosis Diath. Haemorrh. Suppl. 35, 61 (1969). For this purpose, plasma obtained from blood anti-coagulated with 0.01 mole/l of EDTA is adsorbed on Ca phosphate, and the solid is centrifuged off. Thus, the factors are quantitatively bound to the adsorbent and can be recovered by several elutions with 0.2 mole/l of trisodium citrate. The combined eluates are further purified by combined alcohol and acetic acid precipitations at temperatures from $-8°$ C. to $+4°$ C. At the same time, the factors are thus concentrated.

The concentrate is taken up at a pH of 7.5 in a suitable buffer, preferably sodium chloride/sodium citrate in concentrations of 0.06 and 0.02 mole/l respectively.

Those skilled in the art are familiar with the activity determinations.

For Factor IX, this can be carried out, for example, by the following process:

One part, for example 0.1 ml of partial thromboplastin, for example as prepared according to German Auslegeschrift No. 2,316,430, one part of plasma deficient in Factor IX, and one part of diluted normal plasma are mixed. This mixture is kept for 36 minutes at $+37°$ C. Subsequently, one part of a 0.025 molar calcium chloride solution preheated to 37° C. is added and the time is determined which elapses until a clot appears. For quantitative data, the clotting time resulting with the solution containing Factor IX is read off by reference to a calibration curve obtained with a dilution series of normal plasma.

One international unit (IU) of Factor IX corresponds to the Factor IX activity of 1 ml of normal plasma.

Factor X can be determined, for example, by the method of Duckert, F. et al., Blood Coagulation, Hemorrhage and Thrombosis, Ed. Tocantins, L.M. and Kazal, L.A. (1964). For this purpose, one part, for example 0.1 ml of plasma deficient in Factor X, and one part of diluted normal plasma are mixed. This mixture is kept for 30 seconds at $+37°$ C. Subsequently, two parts of calcium-containing thromboplastin prepared, for example, according to German Patent 2,356,493 are added and the time is determined which elapses until a clot appears. For quantitative data, the clotting time resulting with the solution containing Factor X is read off by reference to a calibration curve obtained with a dilution series of normal plasma.

One unit of Factor X corresponds to the Factor X activity of 1 ml of normal plasma.

To destroy the hepatitis viruses, calcium ions and glycine and sucrose are added to the solution and the whole is heated.

For further purification, the heated solution is centrifuged if necessary, and impurities are removed by precipitation with 30–45% weight/volume of ammonium sulfate.

The supernatant liquid is adsorbed on 0.04 to 1.0% weight/volume of calcium phosphate, the charged adsorbent is washed and eluted with citrate buffer, and the eluate is dialysed.

For administration to humans, the product is subjected to sterilization by filtration.

The invention particularly relates to a hepatitis-safe preparation of Factors IX and/or X, which is obtained by this process.

To increase the storage stability, it is advantageous to add protein-stabilizing substances, for example proteins, aminoacids or carbohydrates, to the preparation. Finally, the preparation which has been subjected to this treatment can be made available in a freeze-dried form, and in this case an addition of anti-coagulants, such as, for example, heparin, can be advantageous.

In a solution suitable for pharmaceutical administration, the product according to the invention is a medicament for the treatment of coagulopathy, and it can be used intravenously, advantageously as an infusion, for the therapy and prophylaxis of hemorrhages caused by deficiencies in Factor IX and/or Factor X.

The invention will be explained in more detail by the examples which follow:

EXAMPLE 1

Preparation of a hepatitis-safe concentrate of Factors IX/X from human citrate plasma:

250 g of an anion exchanger (Type A50 Sephadex-DEAE) are added to 500 liters to citrate plasma, and the mixture is stirred for 60 minutes. After sedimentation of the adsorbent, the supernatant plasma is siphoned off and the residue is washed with 20 liters of 0.85% strength NaCl solution.

The absorbent is eluted with 7.5 liters of 1 mole/l NaCl solution at pH 8.0 and is then discarded. 1.2 kg of glycine, 11.2 kg of sucrose and 0.55 kg of $CaCl_2.2H_2O$ are added to the eluate, and the mixture is heated for 10 hours at 60° C. at pH 7.6. After cooling, the mixture is diluted with 50 liters of distilled water and brought to an ammonium sulfate concentration of 40% weight/volume. The precipitate is centrifuged off and discarded. 0.5 kg of Ca phosphate are added to the supernatant liquid which is left to stand for 30 minutes at pH 7.6. After centrifuging, the supernatant liquid is discarded and the adsorbent is washed with two 10 liter portions of 0.5 mole/l NaCl solution. The adsorbent is eluted with 1.8 liters of buffer of pH 8.0, which contains 0.2 mole/l of trisodium citrate, 0.15 mole/l of NaCl, 2 g/100 ml of glycine, 0.3 U/ml of antithrombin III and 14 IU/ml of heparin. After the addition of 0.2 g/100 ml of colloidal silica as a centrifuging aid, the eluate is separated from the adsorbent by centrifuging at 30,000 g. The residue is discarded and the supernatant liquid is dialyzed for 3 hours against 100 liters of a buffer of pH 7, containing 0.06 mole/l of NaCl, 0.02 mole/l of trisodium citrate and 2 g/100 ml of glycine. The dialyzate is tested for the activity of Factors IX and X, adjusted to the desired concentration, sterilized by filtration, divided into unit doses and lyophilized.

About 250 dosage units, each of 200 units of Factor IX, are obtained from 500 liters of plasma.

EXAMPLE 2

Heating of a Factor IX complex concentrate, produced by the process of Soulier et al. [Thromb. Diath. Haemorrh., Suppl. 35, 61, 1969], for inactivating the hepatitis viruses:

The lyophilized product from 4 dosage units of prothrombin complex concentrate, each having about 200 units, is taken up in 20 ml of an aqueous solution which contains 2.2 moles/l of glycine, 1 g/ml of sucrose and 0.5 mole/l of calcium chloride. The pH value is 7.6. After complete dissolution, the container is sealed airtight and incubated for 10 hours at 60° C. in a water bath. After cooling, the mixture is diluted with 160 ml of distilled water and brought to saturation with 40% weight/volume of ammonium sulfate. The precipitate is centrifuged off and the supernatant liquid is adsorbed on 0.8 g of Ca phosphate.

All the further steps are carried out corresponding to Example 1, taking into account the quantitative ratios which are transferable.

We claim:

1. A method for making a preparation containing at least one member selected from the group consisting of blood clotting Factor IX and blood clotting Factor X virtually hepatitis-safe, which method comprises warming said preparation in the presence of an effective amount of calcium ions and in the further presence of an effective amount of at least one member selected from the group consisting of amino acids, saccharides, and sugar alcohols.

2. A method as in claim 1 wherein calcium ions are present in said preparation at a concentration from 0.05 mole/liter to 2.0 moles/liter.

3. A method as in claim 2 wherein said warming is at a temperature from 30° C. to 100° C. for 1 minute to 48 hours in the additional presence of 1.0 mole/liter to 3.0 moles/liter of at least one amino acid selected from the group consisting of glycine, $\alpha$-alanine, $\beta$-alanine, hydroxyproline, proline, glutamine, and $\alpha$-, $\beta$-, and $\gamma$-aminobutyric acids, and of 20 to 60 percent by weight of a member selected from the group consisting of monosaccharides, oligosaccharides, and sugar alcohols.

* * * * *